(12) United States Patent
Cook et al.

(10) Patent No.: US 12,279,986 B2
(45) Date of Patent: Apr. 22, 2025

(54) RECIPROCATING CONNECTING BAR ASSEMBLY FOR A CLUBFOOT BRACE

(71) Applicant: University of Iowa Research Foundation, Iowa City, IA (US)

(72) Inventors: Thomas M. Cook, Iowa City, IA (US); Nicole M. Grosland, Iowa City, IA (US); Jose Morcuende, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 538 days.

(21) Appl. No.: 17/017,160

(22) Filed: Sep. 10, 2020

(65) Prior Publication Data

US 2021/0069003 A1  Mar. 11, 2021

Related U.S. Application Data (60) Provisional application No. 62/898,099, filed on Sep. 10, 2019.

(51) Int. Cl.
*A61F 5/01* (2006.01)
*A61F 5/14* (2022.01)
*A61F 5/37* (2006.01)

(52) U.S. Cl.
CPC .............. *A61F 5/14* (2013.01); *A61F 5/0127* (2013.01); *A61F 5/3715* (2013.01)

(58) Field of Classification Search
CPC .... A61F 5/0127; A61F 5/3715; A61F 5/0102; A61F 5/01; A61F 5/0585; A61F 5/05841; A61F 5/058; A61F 5/14; A61F 5/0111; A61F 5/0116; A61F 5/0195; A61F 5/0193; A43B 7/00; A43B 3/30

USPC ...................................... 602/29, 24
See application file for complete search history.

(56) References Cited

U.S. PATENT DOCUMENTS

| | | | | |
|---|---|---|---|---|
| 2,906,261 A * | 9/1959 | Craig | ................... | A61F 5/0193 602/24 |
| 4,303,065 A * | 12/1981 | Ericson | ................. | A61F 5/0193 602/24 |
| 4,412,536 A * | 11/1983 | Kurtz | ................... | A61F 5/0193 602/24 |
| 4,606,334 A * | 8/1986 | Salmon | ................. | A61F 5/0193 602/24 |
| 7,569,023 B2 | 8/2009 | Dobbs | | |
| 2015/0141893 A1* | 5/2015 | Grosland | .............. | A61F 5/0127 602/29 |

OTHER PUBLICATIONS

Kuhl et al., "Clubfoot Kickbar: Development of an Improved Brace for Use Following Correction of Clubfoot," Proceedings of the 2020 Design of Medical Devices Conference, Apr. 6, 7-9, 2020, Minneapolis, MN, USA.

* cited by examiner

*Primary Examiner* — Victoria Hicks Fisher (74) *Attorney, Agent, or Firm* — Stephen J. Kenny; Foley Hoag LLP (57) ABSTRACT

An apparatus for treating clubfoot is provided that includes a pair of vertically stacked and parallel cross bars that are connected to shoe attachment member via four hinges to define a parallelogram shaped gap therebetween. As the user raises a knee, one shoe attachment member can be displaced via the hinges (primarily in the y-axis or anterior/superior plane) relative to the other shoe attachment member, while the distance between the crossbars remains constant.

16 Claims, 7 Drawing Sheets

RECIPROCATING CONNECTING BAR ASSEMBLY FOR A CLUBFOOT BRACE

CROSS-REFERENCE TO RELATED APPLICATIONS

This application claims the benefit of priority under 35 USC 119 to U.S. Application No. 62/898,099 filed Sep. 10, 2019, the entire contents of which are hereby incorporated by reference.

Embodiments of the present disclosure relate to devices and methods for treating clubfoot. Particularly, the present disclosed subject matter is directed toward a connecting bar assembly for a clubfoot brace.

BRIEF SUMMARY

According to embodiments of the present disclosure, devices and methods for treating clubfoot are provided.

In an exemplary embodiment, the apparatus includes a first shoe attachment member, the first shoe attachment member configured to releasably attach to a shoe; a second shoe attachment member, the first shoe attachment member configured to releasably attach to a shoe; a first crossbar extending between the first shoe attachment member and the second shoe attachment member; a second crossbar extending between the first shoe attachment member and the second shoe attachment member, with the second crossbar disposed vertically below, and parallel to, the first cross bar; a first hinge rotabably coupling the first shoe attachment to the first crossbar; a second hinge rotabably coupling the second shoe attachment to the first crossbar; a third hinge rotabably coupling the first shoe attachment to the second crossbar; and a fourth hinge rotabably coupling the second shoe attachment to the second crossbar.

In some embodiments, the crossbars, shoe attachments and hinges are configured to define a parallelogram-shaped gap therebetween, and the distance between crossbars remains constant throughout the entire range of motion of the apparatus.

In some embodiments, at least one crossbar is rigid (e.g. planar) with a fixed shape, and each crossbar is identical in shape.

In some embodiments, at least one hinge is disposed within a housing.

In some embodiments, the first shoe attachment member can be displaced, relative to the second shoe attachment member, only in the x-axis and y-axis.

In some embodiments, a proximal end of the first shoe attachment member is disposed between the first crossbar and the second crossbar.

In some embodiments, the first crossbar is coupled to the second crossbar.

In some embodiments, the shoe attachment has a slot for releasably receiving a shoe.

The present disclosure also includes an apparatus for treating clubfoot comprising: a first shoe attachment member, the first shoe attachment member configured to releasably attach to a shoe; a second shoe attachment member, the first shoe attachment member configured to releasably attach to a shoe; a first crossbar extending between the first shoe attachment member and the second shoe attachment member; a second crossbar extending between the first shoe attachment member and the second shoe attachment member, with the second crossbar disposed vertically below, and parallel to, the first cross bar; a first hinge rotabably coupling the first shoe attachment to the first crossbar; a second hinge rotabably coupling the second shoe attachment to the first crossbar; a third hinge rotabably coupling the first shoe attachment to the second crossbar; a fourth hinge rotabably coupling the second shoe attachment to the second crossbar; wherein the first shoe attachment member is moveable relative to the second shoe attachment member; and wherein the crossbars, shoe attachments and hinges are configured to define a gap therebetween, the gap retaining a parallelogram-shape throughout the range of motion of the shoe attachment members.

In some embodiments, the first crossbar remains parallel to the second crossbar throughout the entire range of motion of the apparatus.

In some embodiments, each crossbar is identical in shape.

In some embodiments, at least one hinge is disposed within a housing.

In some embodiments, the first hinge and third hinge are disposed within a common housing.

In some embodiments, the first hinge and third hinge are aligned vertically.

In some embodiments, the first shoe attachment member can be displaced, relative to the second shoe attachment member, in the x-axis and y-axis.

In some embodiments, a proximal end of the first shoe attachment member is disposed between the first crossbar and the second crossbar.

DETAILED DESCRIPTION

A variety of methods and/or products are known for treating clubfoot in children. Among them is the Ponseti method, which is a manipulative technique whereby a patient's affected feet are set in a consecutive series of casts that gradually align the feet to their proper position. In some forms of the Ponseti method, the casts are changed weekly, with approximately 4-7 casts worn in total. Following the casting process, the patient will often wear a brace in order to maintain the results of the casting process and prevent the feet from relapsing into a deformed state. The brace can comprise adjustable shoes attached to a connecting bar in such a way so as to maintain the feet at abducted and dorsiflexed angles and maintain a particular position of the feet relative to each other and to the rest of the patient's body. The shoes can be adjusted to a user's feet via a variety of methods, such as laces, buckles, or Velcro. The shoes are often worn for 23 hours a day for a period of a few months, after which they are worn while the patient naps and at night for a period of a few years, typically until the patient is 3-4 years old.

In conventional techniques, a single rigid bar binds the patient's shoes together, allowing no motion or rotation of the feet relative to each other. This lack of motion can cause discomfort for the patient, which can lead to the patient not wearing the brace for as long as prescribed, and eventually relapsing into a deformed positioning of the patient's feet. There thus remains a need for a more comfortable and more tolerable product for maintaining the proper positioning of the feet while also allowing for a greater range of motion.

The present disclosure provides for a connection system for incorporation into a brace (or "foot abduction orthosis") that allows for a particular motion of the feet relative to each other, while also preserving the correction (i.e. orientation relative to the lateral-medial plane) of the feet. In some embodiments, the connection system includes a dual-bar apparatus attached to a pair of shoes, including a first shoe and a second shoe, that allows the patient to move their feet in a particular direction, while still maintaining the proper abduction angle of the feet in relation to each other and to the rest of the patient's body. In some embodiments, the allowed direction of motion is primarily in the up/down (inferior/superior) direction, with motion in the forward/backwards (anterior/posterior) direction inhibited or prohibited. Additionally or alternatively, in some embodiments, rotation of the feet in some directions can be inhibited or prohibited. It will be appreciated that the allowed range of motion of the feet can promote greater comfort when wearing the brace, and lead to higher compliance with wearing the brace for the prescribed number of hours. The range motion of the feet in the brace also allows a patient to stretch the anatomical structures of their legs, which can relieve the patient of pain or discomfort that can result from wearing the brace. Further, it enables the patient to kick and crawl, which will aid in the patient's development.

In embodiments of the present disclosure, a connecting bar apparatus is attached to a pair of shoes, with each of the first shoe and the second shoe of the pair attached to opposing ends of the bar. The connecting bar apparatus can comprise a plurality of shoe attachment pieces and crossbars. The shoes can be fitted to the feet of a patient undergoing clubfoot treatment. In some embodiments, the connecting bar apparatus is attached to each of the first and second shoes on each end via a shoe attachment piece. In some embodiments, two or more joints connect the ends of two or more crossbars to the shoe attachment pieces. In some embodiments, the shoe attachment pieces are attached to the first and second shoes of the brace in a manner that allows for no motion of the first and second shoes relative to the shoe attachment piece.

FIGS. 1-7 show various aspects of exemplary devices for treating clubfoot. In use, a pair of shoes fitted to the user's feet can be attached to the device and worn by the user. A connecting bar apparatus comprising a plurality of shoe attachment pieces and crossbars is attached to the first shoe and the second shoe of the pair of shoes. The device is simple to use and adjust, and can accommodate any size shoe. Advantages of the device include simplicity and in some embodiments, limited adjustability, thereby facilitating use by relatively untrained users. A device like the ones shown in FIGS. 1-7 can be ideal for use where physician access is limited, e.g. in the developing world and rural environments. The simplicity of the design can result in low manufacturing costs. And because the device is simple to use, it does not require careful adjustment by a trained medical professional, whose services may be difficult to obtain in developing communities.

Figure 1:
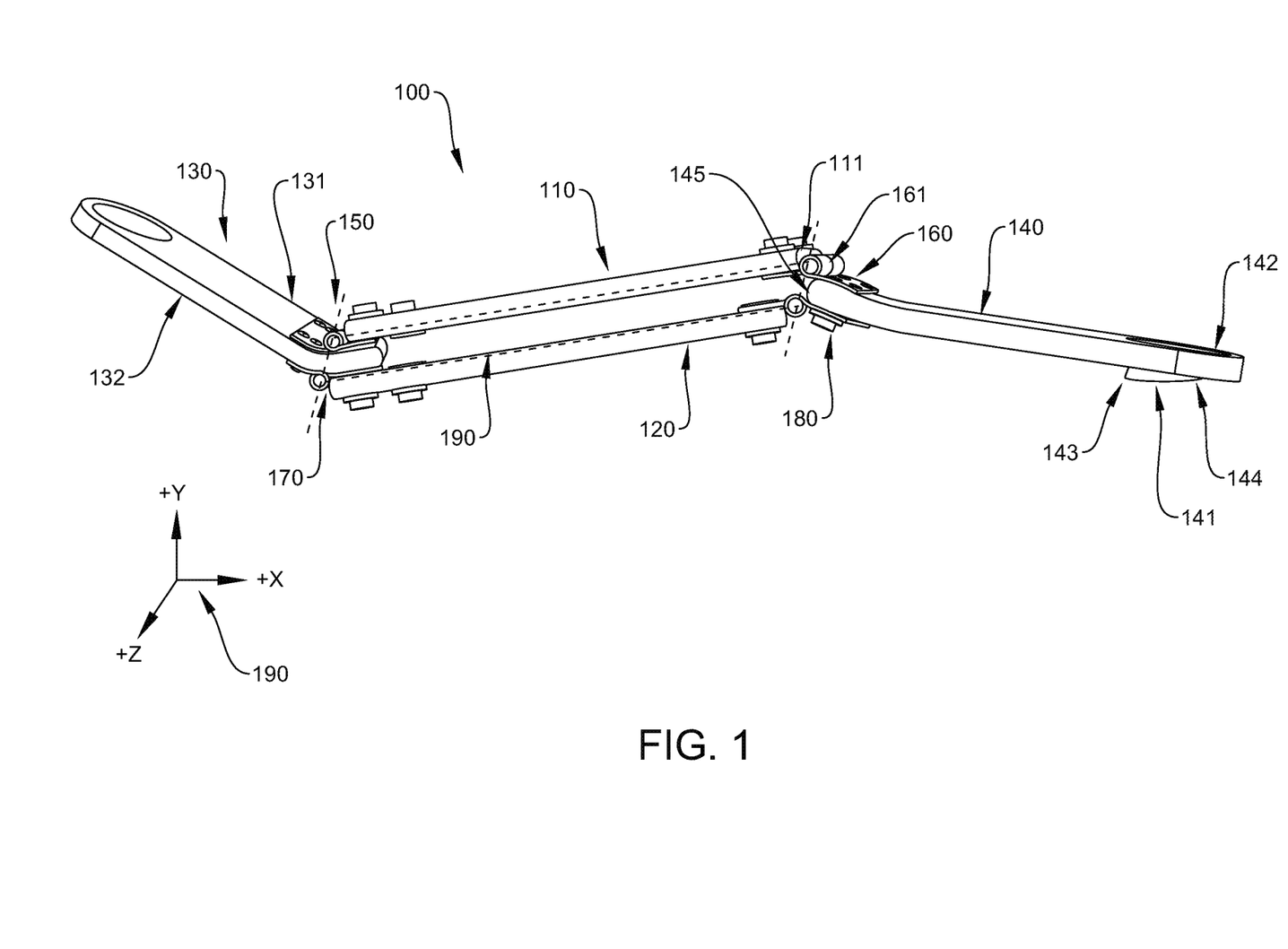
FIG. 1 depicts a front view of an exemplary reciprocating connecting bar apparatus for treating clubfoot, viewed from the front, according to embodiments of the present disclosure.

According to the present disclosure, references to particular directions (e.g., x, y, or z axes) are made with reference to compass 190 in FIG. 1. In compass 190, the y axis is to be understood as the axis from a standing user's feet to their head, the x axis is to be understood as being along the mediolateral axis of a standing user, and the z axis is to be understood as being along the anteroposterior axis of a standing user.

In the present disclosure, some features of the device are discussed for one shoe, foot, or side of the device (e.g., a left or right side). It should be noted that this is for convenience, and it will be appreciated by those skilled in the art that discussions of shoe or side can be similarly applied to the other shoe or side, as the device can be made substantially symmetrical about the yz plane.

With reference now to FIG. 1, a connecting bar apparatus of a device for treating clubfoot, viewed from the front, is shown according to embodiments of the present disclosure. Connecting bar apparatus 100 comprises crossbars 110 and 120, shoe attachment pieces 130 and 140, and joints 150, 160, 170, and 180. Crossbars 110 and 120 are connected at one end to shoe attachment piece 130 by hinges 150 and 170, respectively, and at the other end to shoe attachment piece 140 by hinges 160 and 180, respectively. In various embodiments, hinges 150 and 170 may be vertically aligned. In various embodiments, hinges 160 and 180 may be vertically aligned. This allows for relative motion of the feet in the XY plane, and not in the Z direction, as indicated by compass 190 (movement of user's feet in the z-direction would require pivoting at the hip/waist). FIG. 1 shows the apparatus 100 from the point of view of a user looking face-on at the apparatus. They axis points in the up/down direction of a user, i.e. from a standing user's feet to their head.

According to some embodiments of the present disclosure, the connecting bar apparatus is symmetrical about the x and/or y axes. This allows for easier installation into a brace.

According to some embodiments of the present disclosure, a crossbar is a rigid, unitary piece. In some embodiments, the crossbar is adapted to be placed between the feet of a patient, and is longest in the axis between the patient's feet (the x axis), and shorter in its other dimensions. In some embodiments, the crossbar is fitted with holes adapted to receive a fastener to attach to a hinge or joint, or to directly attach to a shoe attachment piece. In some embodiments, the holes are on the ends of the crossbar in the x axis, and are made parallel to the y axis (so as to extend through the thickness of the crossbar). However, it will be appreciated that the holes can be made in the anteroposterior direction or any other direction.

A shoe attachment piece is a rigid piece adapted to be attached to the bottom of a shoe in a clubfoot brace. In some embodiments, a shoe attachment piece comprises a mechanism for attaching to the bottom of a shoe in a manner that will remain attached during the course of everyday activities, yet can be manually removed without much difficulty, so as to facilitate easy wearing and removing of the brace. In some embodiments, the shoe attachment piece is constructed so that when attached to the shoe, there is no relative motion between the shoe attachment piece and the shoe itself Examples of shoe attachment piece designs are disclosed in U.S. Pat. No. 10,045,874, the entire contents of which are hereby incorporated by reference. The shoe attachment piece can be formed of a rigid material that transfers force directly from the foot through the shoe, and in turn, through the shoe attachment piece and into the crossbars 110, 120.

Alternatively, the shoe attachment piece can be formed of an elastic material, allowing portions of the shoe attachment piece to bend or deflect from the rest of the piece. In such embodiments, the shoe attachment piece can comprise a cantilever, such as cantilever 720 shown in FIG. 7. The shoe attachment piece 140 can be releasably attached to a shoe via a mechanical coupling, e.g. tongue and groove slots, interference fit, male/female union, etc. In some embodiments, the shoe attachment piece 140 has an aperture located near its distal end 142, which is configured to matingly receive a male projection on the sole of the shoe. Additionally or alternatively, in some embodiments, such as the one shown in FIG. 1, the shoe attachment piece 140 attaches to a shoe via a mechanism comprising push button 141 at the end of a cantilever near the distal end 142 of the shoe attachment piece. In such embodiments, the button 141 can comprise a raised surface that protrudes (e.g. downwardly in the y-direction) from the surface of the cantilever.

In some embodiments, shoe attachment pieces 130 and 140 are identical and reversible, with no differences between the one used on the left and the one used on the right. This can minimize the number of unique parts needed in the device's manufacture, and can simplify production and minimize final costs. It will be appreciated that other components can also be made identical, such as crossbars 110 and 120, as well as the various joints used throughout the device.

In embodiments of the present disclosure, a shoe can have a bottom (such as shoe bottoms 570 and 580 in FIGS. 5-6) adapted to receive the distal end of a shoe attachment piece (such as distal end 142 of shoe attachment piece 140). In some embodiments, the shoe bottom comprises a slot in the xz plane to receive the distal end of the shoe attachment piece. In some embodiments, the shoe bottom has an aperture adapted to receive a push button (such as push button 141). As the distal end is inserted into the slot, the cantilever bends until the push button is fully aligned with the aperture on the shoe bottom, at which point the push button enters the aperture, locking the shoe attachment piece in place. The aperture can be accessed by a user, so that a user can push the button through the aperture, thereby releasing the button from the locking position. When the button clears the aperture and is no longer locked into place, the shoe attachment piece can be removed from the shoe by simply pulling the shoe attachment piece.

In some embodiments, the button 141 can comprise a sloped surface with a high end 143 and a low end 144, the high end 143 displaced further from the surface of the cantilever than the low end 144. In such embodiments, in order to attach the shoe attachment piece to the shoe, the distal end 142 of the shoe attachment piece is advanced into a receiving portion of the shoe bottom comprising a locking hole adapted to fit the button. The button slides into the hole with the low end 144 first, and when the high end 143 enters the hole, the button clicks into place, thereby attaching the shoe attachment piece 140 to the shoe. To remove the shoe attachment piece 140, a user can depress the button 141 until the high end 143 clears the locking hole, and pull out the shoe attachment piece 140.

On the interior, opposite end 145 of the shoe attachment piece 140, the shoe attachment piece is adapted to connect to a plurality of, e.g. two, crossbars. In some embodiments, the interior end 145 of the shoe attachment piece is fitted with holes adapted to receive a fastener to attach to a hinge or a joint, or to directly attach to a crossbar. In some embodiments, a proximal end of the shoe attachment piece may be disposed between the cross bars, such as between a first and second crossbar.

A variety of materials can be used for the components of apparatus 100. In some embodiments, materials are chosen that are strong enough to sustain the weight of the wearer and the stresses of daily use. Materials resistant to temperature and weather changes can also be used. Examples of materials used for the crossbars, shoe attachment pieces, and hinges include metal, plastic, or composites such as reinforced plastic. Materials can be formed via a variety of processes, e.g., 3D printing, injection molding, or urethane casting.

It will be appreciated that a variety of mechanical joints can be used to connect the crossbars to the shoe attachment pieces. For example, an end of the crossbar and a shoe attachment piece can be connected by a hinge, knuckle joint, pin joint, or a ball and socket joint adapted to allow for rotation in only one 2-dimensional plane (e.g., about the x-axis and y-axis, with movement along the z-axis inhibited or prohibited). In some embodiments, the joints used to attach the crossbars to the shoe attachment pieces are incorporated into the crossbars and shoe attachment pieces, whereby the connecting ends of the crossbars and shoe attachment pieces are formed as complementary halves of a joint. A pin or bolt can then be used to hold the two halves together. In some embodiments, the joint is a separate piece, which is then fastened to a crossbar on one end and a shoe attachment piece on the other. In some embodiments, such as the one shown in FIG. 1, the joints 150 and 170, and 160 and 180 have metal flanges that extend over the superior and inferior surfaces of the shoe attachment pieces 130 and 140, respectively. This can provide additional durability to the connecting bar apparatus.

A variety of fasteners can be used to affix a joint to a crossbar and shoe attachment piece. In some embodiments, the fasteners comprise screws. In other embodiments, the fasteners comprise a nut and bolt, or chemical fastening (e.g. adhesives).

In some embodiments, the connecting bar apparatus 100 comprises two crossbars 110 and 120. In some embodiments, the two crossbars are the same length in the x direction. In some embodiments, the two crossbars are identical, having the same size in all dimensions. In some embodiments, each of the two crossbars 110 and 120 is connected to a first shoe attachment piece 130 on one end and a second shoe attachment piece 140 on the other end. In some embodiments, one of the crossbars is connected to the superior surface of the two shoe attachment pieces (such as surface 131 of shoe attachment piece 130), and the other crossbar is connected to the inferior surface of the two shoe attachment pieces (such as surface 132 of shoe attachment piece 130), so that one crossbar is above the other crossbar in the y axis and and parallel to the other along the x axis. It will be appreciated that in some embodiments, it is also possible to connect the two crossbars to the anterior and posterior surfaces, respectively, of each of the two shoe attachment pieces.

When the two crossbars are attached as in the embodiments of FIG. 1, wherein one crossbar (110) is attached to the superior surface of the shoe attachment pieces 130 and 140, and a second crossbar (120) is attached to the inferior surface of the shoe attachment pieces, the two crossbars are arranged in a stacked configuration wherein the crossbars are separated by a distance or gap in the vertical or y-axis direction. In some embodiments, this gap distance is approximately the thickness, or height along the y-axis, of a shoe attachment piece. In some embodiments, the distance separating the crossbars remains fixed or constant along the entire length of the crossbars. In embodiments where the crossbars have identical length in the x dimension, and identical distances apart from each other in the y dimension at the left and right ends, the shape of the gap formed by the two crossbars and the shoe attachment pieces can be approximately a parallelogram, outlined by the white dashed line 190.

Furthermore, the relative fixed orientation of the cross bars 110 and 120 and shoe attachment pieces 130 and 140 maintains this parallelogram about the entire range of motion by the patient. In other words, as a patient bends a knee(s) to raise or lower one foot relative to the other, the shoe attachment plate pivots about the four hinge(s) to shift the parallelogram within the X/Y plane while maintaining the abduction angle and rotational orientation of both feet. The use of two crossbars increases the strength of the brace while allowing for motion in the directions allowed by the joints.

According to embodiments of the present disclosure, a patient wearing the brace can move a foot in an up and down reciprocating motion by consecutively raising and lowering the knee in a kicking motion, such as by flexion or extension of the hips. In embodiments where the brace comprises two crossbars, and the crossbars are rigid and of equal length, a patient's feet will not only move along the y axis, but will also move somewhat in the x dimension, and the patient's feet will move slightly closer and then further apart in the x dimension with each cycle.

In some embodiments, the length, in the x dimension, of the connecting bar apparatus, comprising the shoe attachment pieces and crossbars, is approximately the width of a user's shoulders. Thus, the relative lengths of the shoe attachment pieces and the crossbars can be modified in keeping with the constraint that the total apparatus length remains approximately the width of the user's shoulders. In some embodiments, the shoe attachment pieces and crossbars are manufactured to certain fixed dimensions, and do not provide for easily adjusting the relative lengths of the crossbars and shoe attachment pieces. In such embodiments, the relative lengths of the crossbars and shoe attachment pieces are determined at the time of manufacture. In some embodiments, the cross bars can be adjustable in length (along the x-axis). For example, the cross bars can be formed with a telescoping construction in which a first segment slidingly receives a second segment to extend or retract the overall length of the cross bars.

It will be appreciated that increasing the length of the shoe attachment pieces (and thus, decreasing the length of the crossbars by a corresponding amount) will provide for a reduced range of motion when compared to the original lengths of the components. Similarly, decreasing the length of the shoe attachment pieces (and thus, increasing the length of the crossbars by a corresponding amount) will provide for an increases range of motion. However, it should be noted that there can be a limit to how much the lengths of the components can be increased or decreased, and considerations are taken to ensure that the structural stability of the device is not compromised, and that the allowed range of motion of the device does not expose a patient to an increased risk of injury or harm.

As a patient grows, the shoe attachment pieces, crossbars, or the entire connecting bar apparatus can be replaced with ones longer in the x dimension, so as to keep the feet at approximately shoulder width.

In some embodiments of the present disclosure, the connecting bar apparatus is designed such that when connected to the first and second shoes of the brace, the bottom of the connecting bar apparatus is either above or level with the bottom of the user's shoes, allowing for a user to stand with both of their shoes touching the ground. In some embodiments, the bottom of the connecting bar apparatus is lower in the y dimension than the shoes, so that when a user wearing the brace stands, their shoes are raised off of the ground, and the weight of their body is supported by the connecting bar apparatus. Various portions of the connecting bar apparatus can be in contact with the ground to support the weight of the user. In some embodiments, the joints, or a housing surrounding the joints, come in contact with the ground and support the forces placed upon the apparatus. In some embodiments, the forces on the apparatus are supported by the crossbars, which can also be in contact with the ground. Accordingly, the cross bars can be formed with an aspect ratio in which the width (along the z-axis) is greater than the thickness (along the y-axis). This increases the surface area of the cross bar in contact with the ground, thereby providing stability to the patient when standing. Allowing the user to stand while wearing the brace will increase mobility while wearing the brace, as well as increase the comfort in wearing the brace, further increasing compliance and proper treatment of the user's clubfoot.

In embodiments of the present disclosure, the proper angle of the feet (the angle made by the intersection of the proximal/distal axis of both feet) with respect to each other is maintained throughout the allowed range of motion. In some embodiments, feet affected with clubfoot are rotated outwards such that the toes point away from the body at an angle of approximately 60-70 degrees, while unaffected feet are pointed outwards at an angle of approximately 30-40 degrees. However, it will be appreciated that a variety of angles are possible for each foot, and can be chosen based on the needs of the patient or the design of the brace's shoes.

The allowed range of motion can be restricted in a variety of ways. In some embodiments, the range of motion is restricted by precisely positioning the points where the shoe attachment pieces and the crossbars attach. The points are positioned in such a way that at the maximum range of motion, the user would not be able to increase the range of motion without breaking the connecting bar apparatus. For example, at the maximum range of motion, a portion of the crossbars can come in contact with a portion of the joints, or shoe attachment pieces, such that the portion of the joints (or shoe attachment piece) interferes with further rotation of the crossbar in the direction, thereby serving as an abutment or stop to preclude further movement of the crossbars.

In some embodiments of FIG. 1, the range of motion is limited to angles in between where an edge of one (or both) of the crossbars comes into contact with a portion of the joint. For example, at a certain angle, edge 111 of crossbar 110 can come into contact with protruding portion 161 of joint 160. At this angle, the crossbar cannot be rotated further in the direction of the joint, as protruding portion 161 interferes with further motion in that direction. In some embodiments, the range of motion is restricted by assembling the connecting bar apparatus such that the proximal end of each shoe attachment piece (the end furthest from the shoe, and thus closest to the crossbars, such as end 145 of shoe attachment piece 140) extends beyond the point at which the crossbars are joined to the shoe attachment piece. The proximal end of each shoe attachment piece can then be tapered in the y direction, forming a wedge. In such embodiments, at the maximum range of motion, the superior or inferior surface of a crossbar comes in contact with the inferior or superior surface, respectively, of a tapered end of the shoe attachment piece, preventing further motion in that direction.

Figure 2:
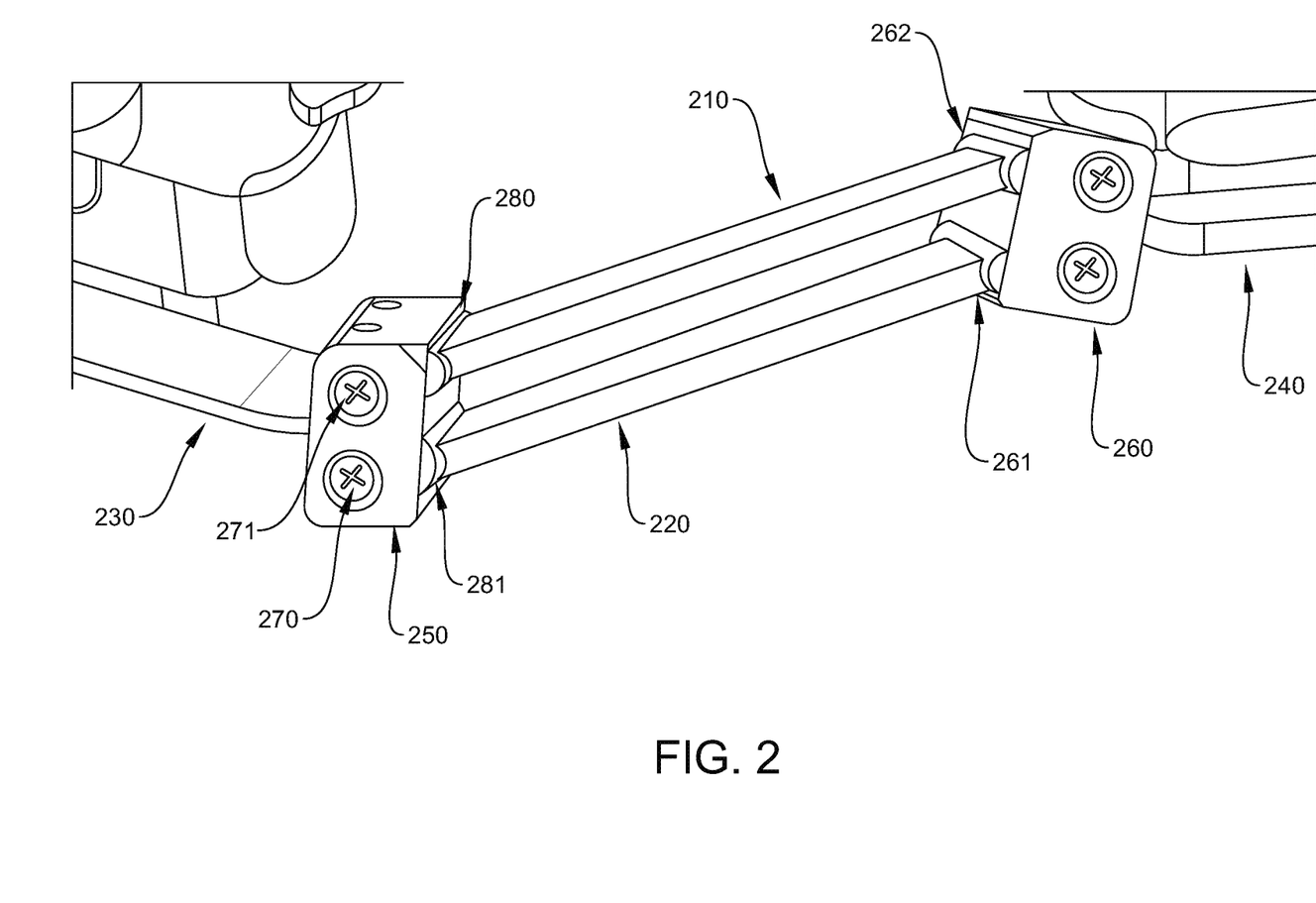
FIGS. 2-3 are zoom in views of the apparatus of FIG. 1.
Figure 3:
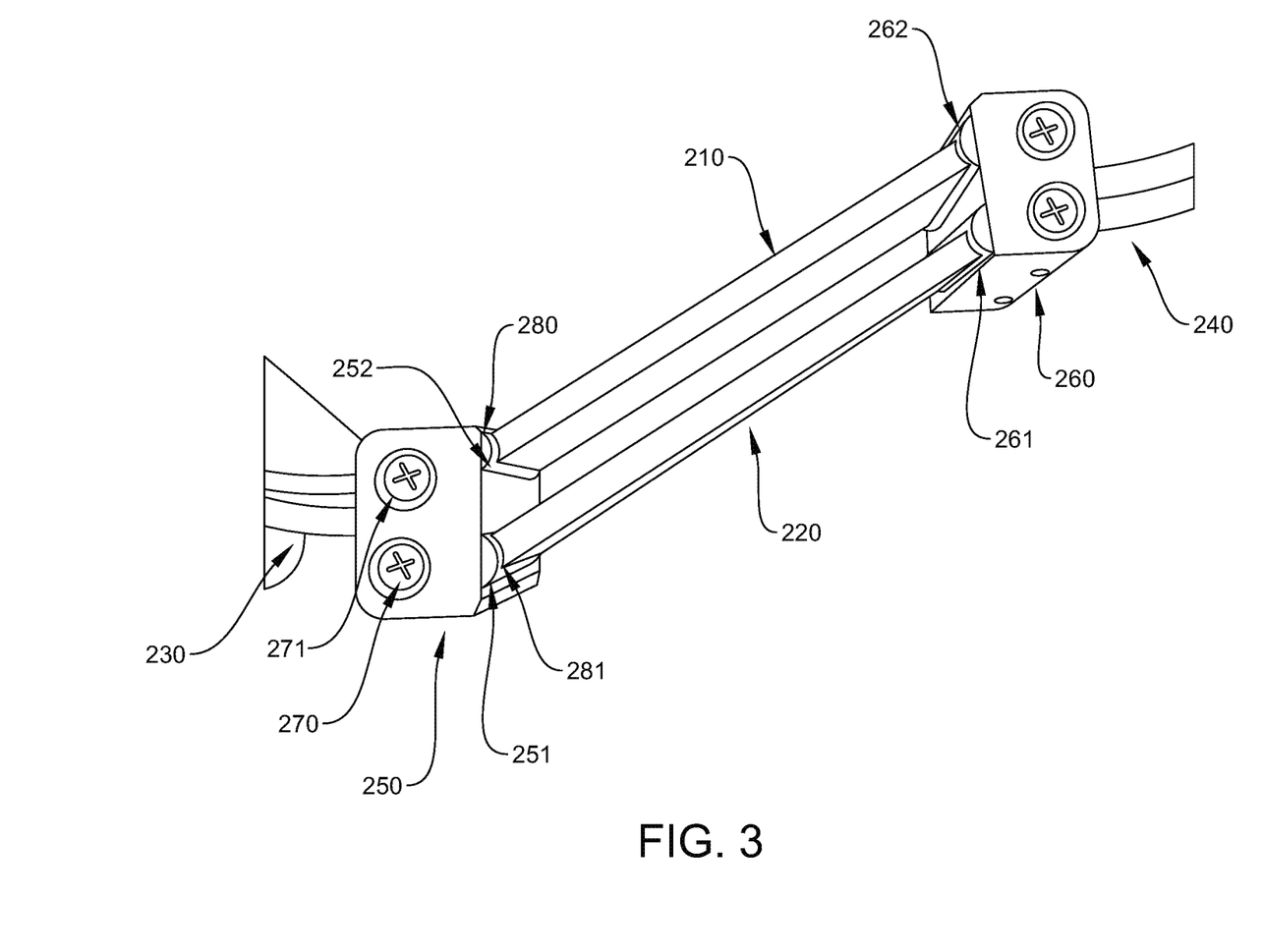

Referring now to FIG. 2, a connecting bar apparatus of a device for treating clubfoot, according to embodiments of the present disclosure is shown. In the embodiment of FIG. 2, a joint is used to connect each end of the crossbars 210 and 220 to the shoe attachment pieces 230 and 240, comprising four joints in total. In FIG. 2, joints 261 and 262 can be seen, surrounded by joint housing 260, while the joint housing 250 obscures the view of the joints 251 and 252 enclosed therein, viewable in FIG. 3. In the embodiments of FIG. 2, the joints are fastened in the direction of the anteroposterior (or z-axis) by fasteners 271 and 270. In some embodiments, the joints are integrated with the shoe attachment piece. In some embodiments, the joints are integrated with the crossbars. In some embodiments, the joints are not integrated with either the shoe attachment pieces or the crossbars, and are attached to the shoe attachment pieces and crossbars via fasteners, as described above. In some embodiments of FIG. 2, the range of motion of the apparatus is limited to angles in between where the top left edge of crossbar 210 strikes the top right edge of joint housing 250 at 280, and where the bottom left edge of crossbar 220 strikes the bottom right edge of joint housing 250 at 281. FIG. 3 depicts an alternative view of the connecting bar apparatus of FIG. 2, shown from the perspective of FIG. 1. It will be appreciated that in some embodiments, the joint housings 250 and 260 can be made so as to support the weight of the apparatus and user, and have a bottom surface large enough to allow a user to stand while wearing the brace.

Figure 4:
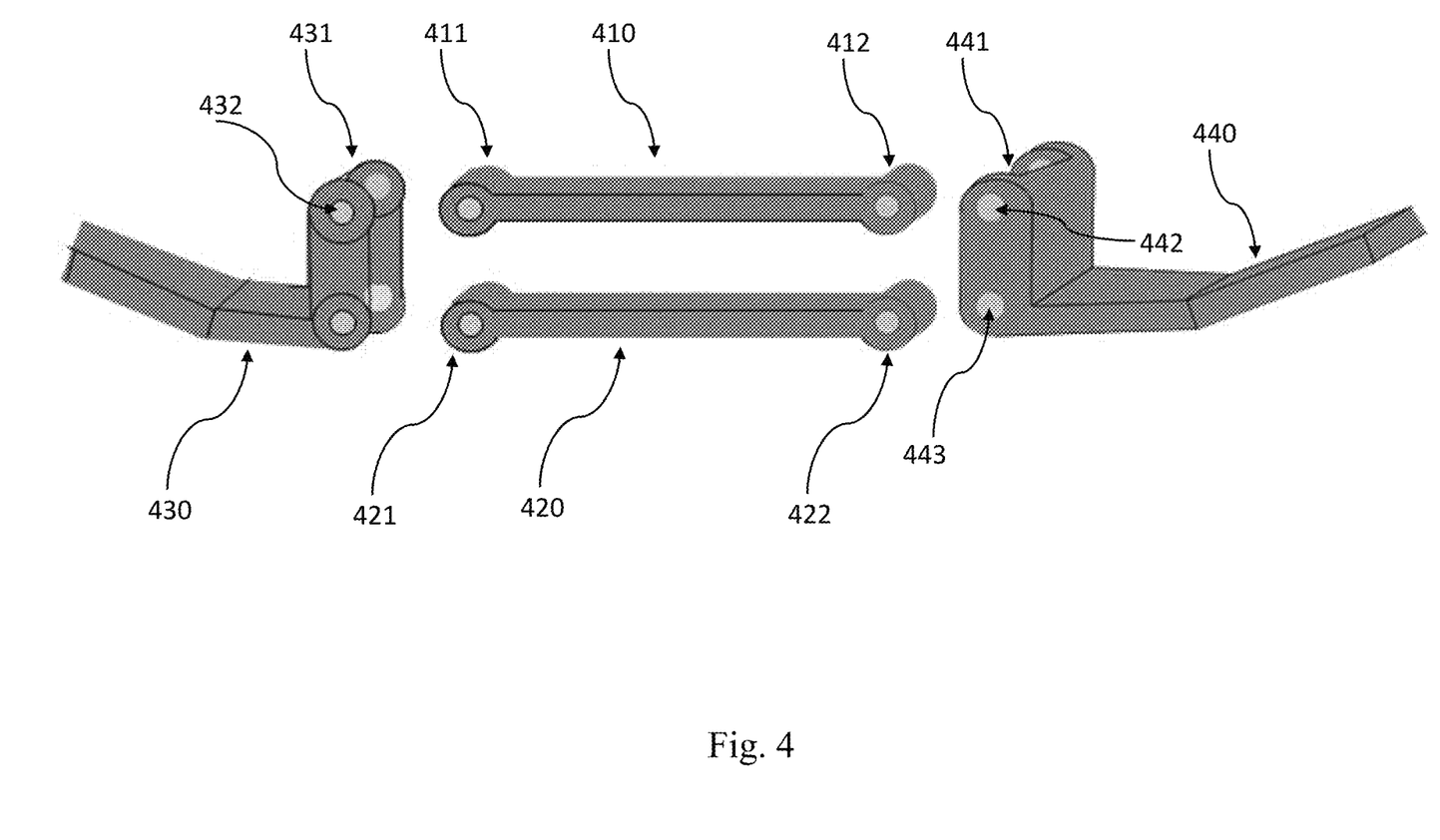
FIG. 4 is an exploded schematic view of the apparatus of FIG. 1.

Referring now to FIG. 4, a schematic view of a connecting bar apparatus of a device for treating clubfoot, according to embodiments of the present disclosure is shown. In embodiments of FIG. 4, the shoe attachment pieces and the crossbars are injection molded. In some embodiments of FIG. 4, the joints are incorporated into the shoe attachment pieces 430 and 440 at 431 and 441, respectively, and into the crossbars 410 and 420 at 411 and 412, and at 421 and 422, respectively. The joints can be connected by inserting a fastener, e.g., a pin or bolt, into the joints at corresponding ends of the crossbars and shoe attachment pieces. For example, a pin or bolt can be inserted through hole 432 to connect joint ends 411 and 431 together, and through hole 442 to connect joint ends 412 and 442 together, thereby connecting shoe attachment pieces 430 and 440 with crossbar 410. It will be appreciated that in embodiments of FIG. 4, the weight of a user can be supported by the shoe attachment pieces 430 and 440 and/or the bottom crossbar 420.

Figure 5:
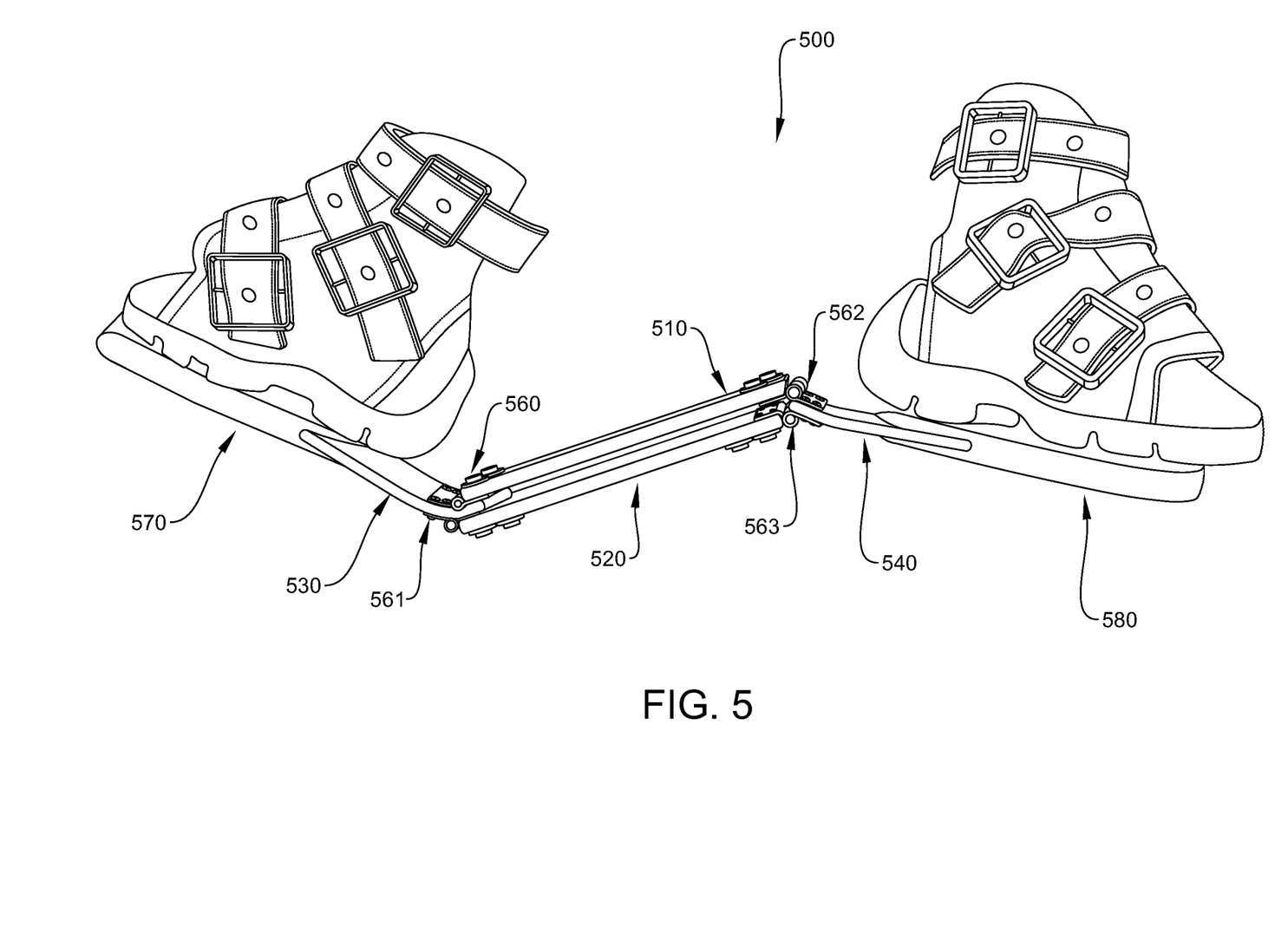
FIG. 5 depicts a front view of the apparatus of FIG. 1, including shoe attachments, according to embodiments of the present disclosure.

Referring now to FIG. 5, a device for treating clubfoot according to embodiments of the present disclosure is shown. Brace 500 is shown with crossbars 510 and 520 connected to shoe attachment pieces 530 and 540 via joints 560 and 561, and 562 and 563, respectively. It will be appreciated that in some embodiments, a patient can stand while wearing brace 500, as when the feet are extended an approximately equal amount, as is typical while standing, the inferior surface of crossbar 520 does not sit below the bottoms of shoes 570 and 580, allowing the patient to stand on the bottom of the shoes in a supported manner.

Figure 6:
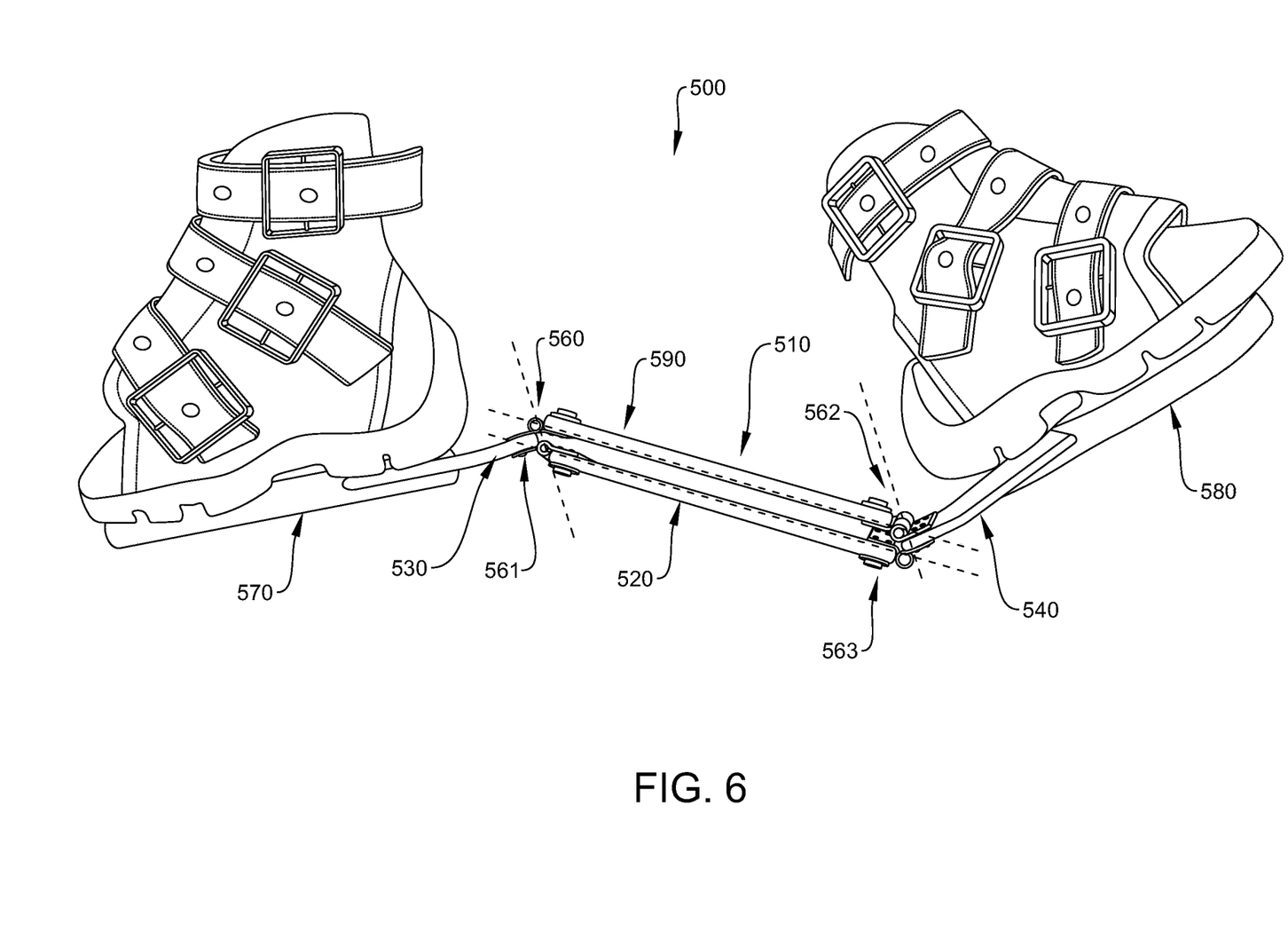
FIG. 6 depicts an alternative view of the device of FIG. 5.

Referring now to FIG. 6, an alternative view of the device of FIG. 5 is shown according to embodiments of the present disclosure. Parallelogram 590 is formed by the two crossbars and the shoe attachment pieces. In embodiments of FIGS. 5-6, the distances between crossbars 510 and 520 between the joints 560 and 561, and 562 and 563 are equal, and remain equal throughout the entire range of motion of the apparatus. In some embodiments, the lengths of the two crossbars in the x dimension are equal.

Figure 7:
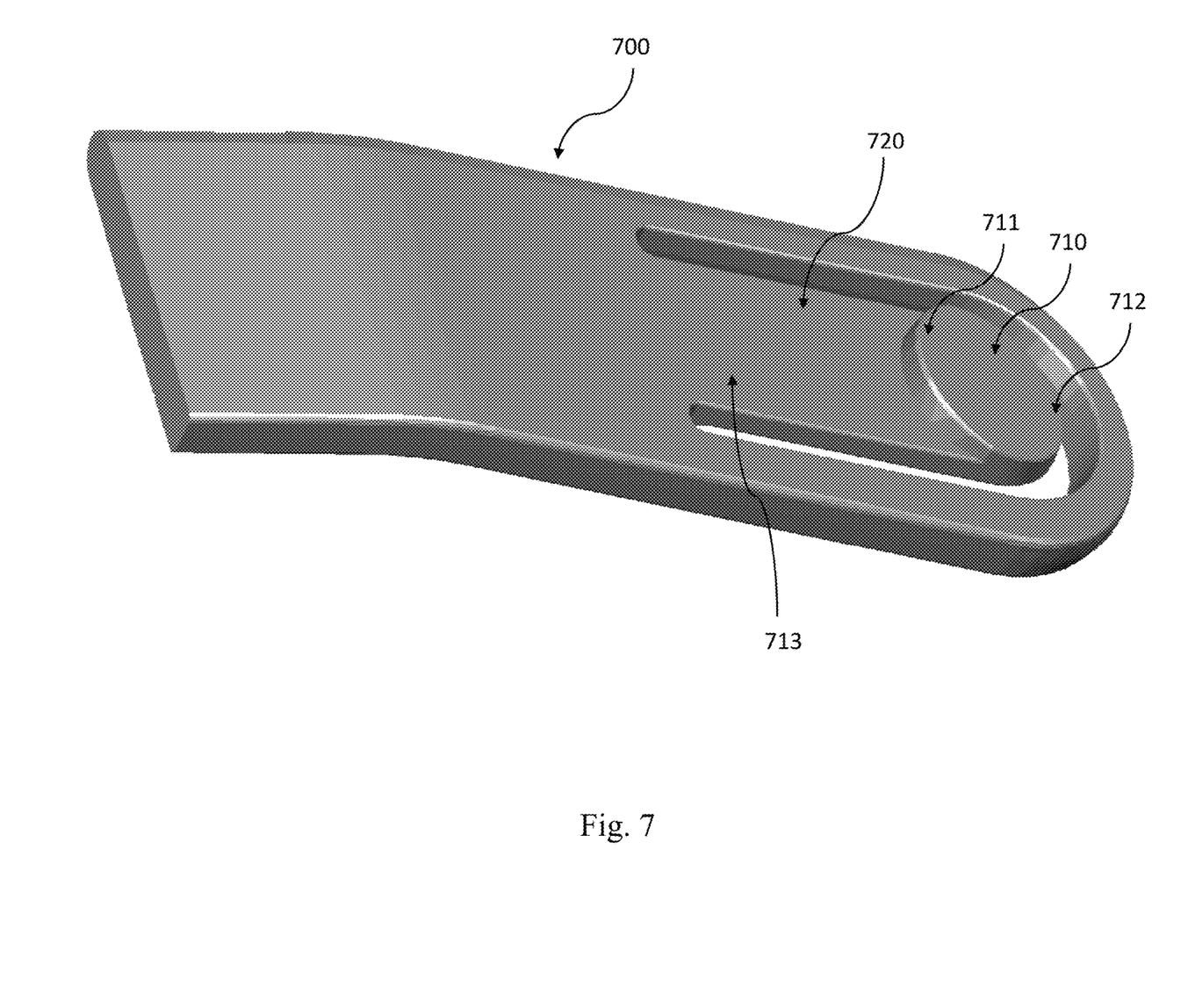
FIG. 7 depicts a close-up view of an exemplary shoe attachment piece according to embodiments of the present disclosure.

Referring now to FIG. 7, a close-up view of a shoe attachment piece according to embodiments of the present disclosure is shown. Distal end 700 of a shoe attachment piece may be inserted into a slot in the bottom of a shoe in a clubfoot brace. Distal end 700 comprises a cantilever 720 with a pushbutton 710 attached on the end, and raised above the surface of the cantilever 720. Connecting member 713 connects the pushbutton to the shoe attachment piece. In some embodiments, pushbutton 710 has a proximal end 711 and a distal end 712, wherein the pushbutton 710 is tapered such that the proximal end 711 is raised above the distal end 712. It will be appreciated that this can facilitate easier attachment of a shoe attachment piece into a shoe. In use, the distal end 700 is inserted into a slot of a shoe. The slot has an aperture around the size of the pushbutton 710. When the distal end of the shoe attachment piece is fully inserted into the slot, the pushbutton enters the aperture and clicks into place, locking the shoe attachment piece in place. To remove the shoe attachment piece, the pushbutton 710 may be pressed until it is no longer within the aperture, whereupon the shoe attachment piece may be pulled out. In some embodiments, connecting member 713 has a length in the x direction smaller than the diameter of the pushbutton 710.

In addition to the specific embodiments described above, the disclosed subject matter is also directed to other embodiments having any other possible combination of the features disclosed above. As such, the particular features disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the exemplary embodiments disclosed herein.

What is claimed is:

1. An apparatus for treating clubfoot in a patient comprising:
   a first shoe attachment member, the first shoe attachment member configured to releasably attach to a first shoe;
   a second shoe attachment member, the second shoe attachment member configured to releasably attach to a second shoe;
   a first crossbar extending between the first shoe attachment member and the second shoe attachment member, defining an x-axis therebetween;
   a second crossbar extending between the first shoe attachment member and the second shoe attachment member, with the second crossbar disposed vertically below the first crossbar, defining a y-axis therebetween, and parallel to the first cross bar, each of the first crossbar and the second crossbar are planar in shape, the x-axis and the y-axis forming a plane;
   a first hinge having a first pin disposed perpendicularly to the plane formed by the x-axis and the y-axis, the first hinge configured to rotatably couple the first shoe attachment member to the first crossbar;

a second hinge having a second pin disposed perpendicularly to the plane formed by the x-axis and the y-axis, the second hinge configured to rotatably couple the second shoe attachment member to the first crossbar;

a third hinge having a third pin disposed perpendicularly to the plane formed by the x-axis and the y-axis, the third hinge configured to rotatably couple the first shoe attachment member to the second crossbar; and a fourth hinge having a fourth pin disposed perpendicularly to the plane formed by the x-axis and the y-axis, the fourth hinge configured to rotatably couple the second shoe attachment member to the second crossbar, wherein the first shoe attachment member can be displaced relative to the second shoe attachment member, only in the plane formed by the x-axis and y-axis while maintaining a constant abduction angle of the first and the second shoe during the displacement via rotation of the first and the second cross members about the first, second third and fourth pins.

2. The apparatus of claim 1, wherein the first and second crossbars, the first and second shoe attachment members and the first, second, third and fourth hinges are configured to define a parallelogram-shaped gap therebetween.

3. The apparatus of claim 1, wherein a distance between the first and second crossbars remains constant throughout the entire range of motion of the apparatus.

4. The apparatus of claim 1, wherein at least one of the first and second crossbars is rigid with a fixed shape.

5. The apparatus of claim 1, wherein each of the first and second crossbars is identical in shape.

6. The apparatus of claim 1, wherein at least one of the first, second, third and fourth hinges is disposed within a housing.

7. The apparatus of claim 1, wherein the first shoe attachment member can be displaced with movement along the z-axis inhibited.

8. The apparatus of claim 1, wherein a proximal end of the first shoe attachment member is disposed between the first crossbar and the second crossbar.

9. The apparatus of claim 1, wherein the first crossbar is coupled to the second crossbar.

10. The apparatus of claim 1, wherein each of the first and second shoe attachment members has a slot for releasably receiving the first shoe and the second shoe, respectively.

11. The apparatus of claim 1, wherein the second hinge and the fourth hinge are aligned vertically.

12. The apparatus of claim 1, wherein the second hinge and the fourth hinge are disposed within a common housing.

13. The apparatus of claim 1, wherein the first hinge and third hinge are disposed within a common housing.

14. The apparatus of claim 1, wherein the first hinge and third hinge are aligned vertically.

15. The apparatus of claim 1, wherein a proximal end of the second shoe attachment member is disposed between the first crossbar and the second crossbar.

16. The apparatus of claim 1, wherein a portion of the first and second crossbars, the first, second, third and fourth hinges and the first and second shoe attachment members are disposed within a housing.

* * * * *